United States Patent [19]

Kaufmann et al.

[11] Patent Number: 5,010,201
[45] Date of Patent: Apr. 23, 1991

[54] PROCESS FOR THE PREPARATION OF SUBSTITUTED 2-CHLOROPYRIDINES

[75] Inventors: Dieter Kaufmann, Bergisch Gladbach; Bernd Gallenkamp, Wuppertal, both of Fed. Rep. of Germany

[73] Assignee: Bayer Aktiengesellschaft, Leverkusen, Fed. Rep. of Germany

[21] Appl. No.: 430,389

[22] Filed: Nov. 1, 1989

[30] Foreign Application Priority Data

Nov. 22, 1988 [DE] Fed. Rep. of Germany ....... 3839332

[51] Int. Cl.$^5$ .......................................... C07D 213/61
[52] U.S. Cl. .................................. 546/316; 546/318; 546/321; 546/323; 546/345; 546/286
[58] Field of Search ............... 546/345, 286, 316, 318, 546/321, 323

[56] References Cited

U.S. PATENT DOCUMENTS 4,211,873  7/1980  Pews et al. ......................... 546/346
4,897,488  1/1990  Gallenkamp et al. ............... 546/345

FOREIGN PATENT DOCUMENTS 0032516  7/1981  European Pat. Off. ............ 546/345
154316   9/1985  European Pat. Off. ............ 546/345
256714   2/1988  European Pat. Off. ............ 546/345
305967   8/1989  European Pat. Off. ............ 546/345
2395262  6/1921  France ................................ 546/346

OTHER PUBLICATIONS

Ichiro Kawase et al., Cancer Research, vol. 48, pp. 1173-1179 (1988).
Preparation of 2-Chloro—3—Cyanopyridine and 2—Chloronicotinic Acid, Apr. 14, 1982, vol. 6, No. 57, p. 935, Patent Abstracts of Japan.
Chemical and Pharmaceutical Bulletin Band 36, No. 6, 1988, pp. 2244-2247; H. Yamanaka et al: Site-Selectivity in the Reaction of 3—Substituted Pyridine 1—Oxides with Phosphoryl Chloride.
Chemistry of the Heterocyclic N-Oxides 1971 Academic Press, London, pp. 260-265; Katritzky et al.
The Synthesis of 2—Chloromethylpyridine from 2—Picoline—N—Oxide, Journal of Heterocyclic Chemistry Band 18, No. 5, Aug. 1981, pp. 939-940.

Primary Examiner—Mary C. Lee
Assistant Examiner—Joseph K. McKane
Attorney, Agent, or Firm—Sprung Horn Kramer & Woods

[57] ABSTRACT

A new process has been found for the preparation of substituted 2-chloropyridine derivatives of the formula (I)

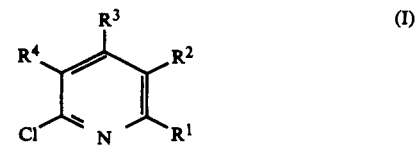

wherein $R^1$ to $R^4$ have the meanings as defined in the description.

The new process is characterized in that pyridine 1-oxides of the formula II

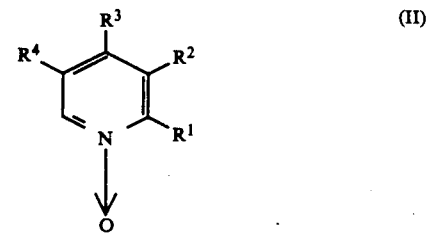

are
  reacted with a chlorine-containing phosphoric acid derivative from the series of the chlorophosphoric esters and chlorophosphoramides in the presence of an inert organic solvent and in the presence of an acid acceptor at temperatures between $-20°$ C. and $200°$ C., and the resulting product is separated further, if appropriate.

Compound (I) is known as an intermediate product for medicaments (cf.DE-A 2,812,585) or for insecticidel nitromethylene derivatives (cf. EP-A 163,855).

9 Claims, No Drawings

PROCESS FOR THE PREPARATION OF SUBSTITUTED 2-CHLOROPYRIDINES

The present invention relates to a new process for the preparation of substituted 2-chloropyridines.

It is known that 2-chloro-5-methyl-pyridine is obtained (besides 2-chloro-3-methyl-pyridine, 4-chloro-3-methylpyridine and 3-chloro-5-methyl-pyridine) on reacting 3-methyl-pyridine 1-oxide with phosphoryl chloride (cf. Weissberger, Chemistry of Heterocyclic Compounds, Pyridine and its Derivatives, Vol. 14, Supplement, Part 2, p. 112, publisher John Wiley & Sons, New York, 1974). The main product of this reaction is 4-chloro-3-methylpyridine; the amount of 2-chloro-5-methyl-pyridine is generally less than 25%

An earlier patent application which is non-prior-published with regard to the present application has as the subject-matter the reaction of 3-methylpyridine 1-oxide with phosphoryl chloride in the presence of a basic organic nitrogen compound and in the presence of a diluent (German Patent Application P 3,800,179 dated 07.01.88).

A new process has now been found for the preparation of substituted 2-chloropyridine derivatives of the formula (I)

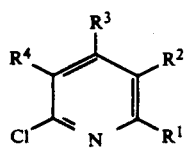

in which $R^1$ represents hydrogen, chlorine, cyano, carbalkoxy-($C_1$–$C_4$) or

where $R^5$ and $R^6$ are identical or different and represent hydrogen or alkyl ($C_1$–$C_4$), $R^2$ represents hydrogen, chlorine, alkyl($C_1$–$C_4$), halogenoalkyl($C_1$–$C_4$), cyanoalkyl($C_1$–$C_4$), alkoxy($C_1$–$C_4$)-alkyl($C_1$–$C_4$), dialkylamino($C_1$–$C_4$)alkyl($C_1$–$C_4$), carbalkoxy($C_1$–$C_4$) or

where $R^5$ and $R^6$ are identical or different and represent hydrogen or alkyl ($C_1$–$C_4$)

or where $R^1$ and $R^2$ together represent the bivalent group —CH=CH—CH=CH—, $R^3$ represents hydrogen, chlorine, carbalkoxy($C_1$–$C_4$) or

where $R^5$ and $R^6$ are identical or different and represent hydrogen or alkyl ($C_1$–$C_4$), and $R^4$ represents hydrogen, chlorine or cyano, or where $R^3$ and $R^4$ together represent the bivalent group —CH=CH—CH=CH—.

The new process is characterized in that pyridine 1-oxides of the formula II

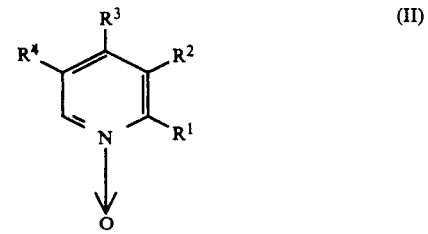

in which $R^1$, $R^2$, $R^3$ and $R^4$ have the abovementioned meaning are reacted with a chlorine-containing phosphoric acid derivative from the series of the chlorophosphoric esters and chlorophosphoramides in the presence of an inert organic solvent and in the presence of an acid acceptor at temperatures between $-20°$ C. and $200°$ C., and the resulting product is separated further, if appropriate.

With the aid of the process according to the invention it is possible, surprisingly, to convert substituted pyridine 1-oxides of the formula (II) into the corresponding substituted 2-chloropyridines of the formula (I) by reaction with chlorophosphoric esters or chlorophosphoramides in the presence of an acid acceptor in a simple manner without complications and with surprisingly high yields.

Other advantages of the process according to the invention, besides the good yield of desired product, are that the amount of isomeric by-products is considerably lower than in the synthesis method known to date. If desired, it is furthermore possible to prepare the pure compound (I) from the reaction product in a straightforward manner by customary methods, for example separation by distillation or other conventional separation methods. The process according to the invention therefore represents a valuable enrichment of the art.

If 3-methyl-pyridine 1-oxide is reacted with N,N-diethyldichlorophosphoramide in the presence of the base diisopropylamine in methylene chloride, the course of the reaction in the process according to the invention can be outlined by the equation below.

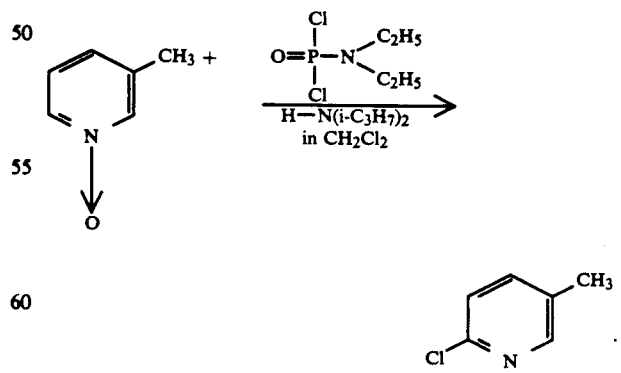

The following may be mentioned as compounds of the general formula (I) which can preferably be prepared using the process according to the invention:

2,3-Dichloropyridine
2,4-Dichloropyridine 2,6-Dichloropyridine
2-Chloro-3-cyano-pyridine
2-Chloro-6-cyano-pyridine
Methyl 6-chloro-pyridine-2-carboxylate
Ethyl 6-chloro-pyridine-2-carboxylate
N,N-Dimethyl-6-chloro-pyridine-2-carboxamide
N,N-Diethyl-6-chloro-pyridine-2-carboxamide
N,N-Diethyl-6-chloronicotinamide
Methyl 2-chloro-pyridine-4-carboxylate
Ethyl 2-chloro-pyridine-4-carboxylate
N,N-Dimethyl-2-chloro-pyridine-4-carboxamide
N,N-Diethyl-2-chloro-pyridine-4-carboxamide
2-Chloro-5-diisopropylaminomethyl-pyridine
2-Chloro-5-diisobutylaminomethyl-pyridine
2-Chloro-5-methyl-pyridine
2,6-Dichloro-3-methyl-pyridine
2-Chloro-5-ethyl-pyridine
2-Chloro-5-chloromethyl-pyridine
2-Chloro-5-cyanomethyl-pyridine
2-Chloro-5-methoxymethyl-pyridine
2-Chloro-5-ethoxymethyl-pyridine
Methyl 6-chloro-nicotinate
Ethyl 6-chloro-nicotinate
N,N-Dimethyl-6-chloro-nicotinamide
2-Chloroquinoline
1-Chloroisoquinoline It is particularly preferred to prepare the following compound of the formula (I):
2-Chloro-5-methyl-pyridine.

The starting materials pyridine 1-oxides of the formula (II) and chlorophosphoric esters or chlorophosphoramides are known compounds of organic chemistry or can be prepared by known processes. See, for example:

Weissberger, Chemistry of Heterocyclic Compounds, Pyridine and its Derivatives, Vol. 14, Supplement, Part 2, p. 112, publisher John Wiley & Sons, New York, 1974.

Methoden der Organischen Chemie [Methods of Organic Chemistry] (Houben-Weyl, Miller), Volume 12, 2, p. 212, 239, 383, 445, Georg Thieme Verlag, Stuttgart, 1964.

Formula (II) provides a general definition of the substituted pyridine 1-oxides which are employed as starting substances for the process according to the invention.

In formula (II), $R^1$ preferably represents hydrogen, chlorine, cyano, $COOCH_3$, $COOC_2H_5$, $CON(CH_3)_2$ and $CON(C_2H_5)_2$, $R^2$ preferably represents hydrogen, chlorine, $CH_3$, $C_2H_5$, $CH_2Cl$, $CH_2CN$, $CH_2-OCH_3$, $CH_2-OC_2H_5$, $CH_2-N(i-C_3H_7)_2$, $CH_2-N(i-C_4H_9)_2$, $COOCH_3$, $COOC_2H_5$, $CON(CH_3)CH_2$ and $CON(C_2H_5)_2$, $R^3$ preferably represents hydrogen, chlorine, $COOCH_3$, $COOC_2H_5$, $CON(CH_3)_2$ and $CON(C_2H_5)_2$ or $R^1$ and $R^2$ in each case together represent the bivalent group —CH=CH—CH=CH— and $R^4$ preferably represents hydrogen, chlorine or cyano, or $R^3$ and $R^4$ in each case together represent the bivalent group —CH=CH—CH=CH—.

3-Methyl-pyridine 1-oxide, in particular, is employed as the starting substance of the formula (II).

The chlorine-containing phosphoric acid derivatives from the series of the chlorophosphoric esters and chlorophosphoramides which are employed in the process according to the invention preferably are from the following classes of compounds:

Monoalkyl chlorophosphates,
Dialkyl chlorophosphates,
Cycloalkyl chlorophosphates,
Aryl chlorophosphates,
Diaryl chlorophosphates,
N-Monoalkyl-chlorophosphoramides,
N,N-Dialkyl-chlorophosphoramides,
N,N,N', N'-Tetralkylchlorophosphoric diamides,
N-Cycloalkyl-chlorophosphoramides,
N-Aryl-chlorophosphoramides and
N,N-Diaryl-chlorophosphoramides.

Compounds which are particularly preferably employed are 1. N,N-dialkyl($C_1$–$C_4$)-chlorophosphoramides and, in particular, N,N-dimethyl-dichlorophosphoramide, N,N-diethyldichlorophosphoramide, N,N-dipropyl-dichlorophosphoramide, N,N-diisopropyl-dichlorophosphoramide, N,N-dibutyl-dichlorophosphoramide and N,N-diisobutyl-dichlorophosphoramide, and 2. alkyl($C_1$–$C_6$) chlorophosphoric esters and, in particular, methyl dichlorophosphate, ethyl chlorophosphate, propyl dichlorophosphate, isopropyl dichlorophosphate, butyl dichlorophosphate, isobutyl dichlorophosphate, tert.-butyl dichlorophosphate, pentyl dichlorophosphate and hexyl dichlorophosphate.

The process according to the invention is carried out using inert organic solvents. Solvents which are suitable for this purpose are virtually all inert organic solvents. These preferably include aliphatic or aromatic hydrocarbons, such as pentane, hexane, heptane, octane, cyclohexane, methylcyclohexane, petroleum ether, benzine, ligroin, benzene, toluene, xylene and tetralin, halogenated hydrocarbons, such as methylene chloride, ethylene chloride, trichloroethylene, chloroform, carbon tetrachloride, chlorobenzene and dichlorobenzene, ethers, such as diethyl ether, dipropyl ether, diisopropyl ether, dibutyl ether, methyl tert-butyl ether, glycol dimethyl ether, diglycol dimethyl ether, tetrahydrofuran and dioxane, ketones, such as acetone, methyl ethyl ketone, diethyl ketone, methyl isopropyl ketone, methyl isobutyl ketone and methyl tert.-butyl ketone, esters, such as methyl acetate, ethyl acetate, propyl acetate, butyl acetate, amyl acetate, dimethyl phthalate and diethyl phthalate, nitriles, such as acetonitrile and propionitrile, amides, such as dimethylformamide, dimethylacetamide and N-methylpyrrolidone, and also dimethyl sulphoxid and tetramethylene sulphone.

Particularly preferred organic solvents are methylene chloride, chloroform and chlorobenzenes.

The reaction according to the invention is carried out in the presence of an acid acceptor. An acid acceptor which is preferably suitable is a basic nitrogen compound. Preferred basic nitrogen compounds are dialkylamines, such as, for example, diethylamine, dipropylamine, dibutylamine, diisobutylamine and di-sec-butylamine, trialkylamines, such as, for example, triethylamine, tripropylamine and tributylamine, dialkylcycloalkylamines, such as, for example, dimethyl-cyclopentylamine, diethyl-cyclopentylamine, dimethyl-cyclohexylamine and diethylcyclohexylamine, or dialkylaralkylamines, such as, for example, dimethylbenzylamine and diethylbenzylamine, and dialkylarylamines, such as, for example, dimethylaniline, and also pyridine derivatives, such as 2,6-dimethylpyridine and 2,4,6-trimethylpyridine.

As the basic organic nitrogen compound, diisopropylamine is particularly preferred.

The process according to the invention is carried out in a temperature range between −20° C. and 200° C., preferably at temperatures between 0° C. and 150° C. The process according to the invention is generally carried out under atmospheric conditions. However, it is also possible to carry out the process under increased or reduced pressure between 0.1 and 10 bar. To carry out the process according to the invention, between 1 and 10 moles, preferably between 1 and 2 moles, of chlorophosphoric ester or chlorophosphoramide, and also between 1 and 10 moles, preferably between 1 and 2 moles, of the basic organic nitrogen compound, are generally employed per mole of substituted pyridine 1-oxide of the formula (II). It is particularly preferred to employ approximately 1.5 moles of chlorophosphoric ester or chlorophosphoramide and nitrogen compound in each case per mole of substituted pyridine-N-oxide.

To carry out the process according to the invention, it is preferred to add dropwise a mixture of a chlorophosphoric ester or chlorophosphoramide and an amine to a solution of the substituted pyridine oxide of the formula (II), and the entire reaction mixture is stirred for several hours at the specific temperature required (preferably in the range of 0° C. and 150° C.).

The mixture can be worked up in the customary manner. After the filtration, the reaction mixture is preferably (a) distilled, (b) extracted or (c) treated with water, the organic solvent is removed, for example by distillation, the aqueous phase is adjusted to a pH of 6 using an aqueous alkali metal hydroxide solution or alkaline earth metal hydroxide solution, such as, for example, sodium hydroxide solution, and most of the reaction product is removed from this mixture by steam distillation. The organic phase of the steam distillate essentially contains the product of the formula (I).

The pure compound of the formula (I) can be prepared from the organic phase of the steam distillate by customary methods, for example by fine-distillation on a packed column. The overall yield in the preparation of 2-chloro-5-methyl-pyridine, starting from 3-methyl-pyridine 1-oxide, is 70 to 83% of theory.

2-Chloro-5-methylpyridine, which can be prepared by the process according to the invention, is known as an intermediate for medicaments (cf. DE-A 2,812,585).

2-Chloro-5-methyl-pyridine can furthermore be employed as an intermediate for the preparation of insecticidal nitromethylene derivatives (cf. EP-A 163,855).

PREPARATION EXAMPLE 1

2-Chloro-5-methylpyridine

A solution of 71.3 g (0.375 mol) of N,N-diethyldichlorophosphoramide and 37.9 g (0.375 mol) of diisopropylamine in 100 ml of methylene chloride is added dropwise to a solution of 27.3 g (0.25 mol) of 3-methylpyridine 1-oxide in 300 ml of methylene chloride. The batch is left to stand for 5 hours at room temperature, the solids are filtered off with suction, the filter cake is washed once using 50 ml of methylene chloride, and the solvent is stripped off in vacuo. 100 ml of water are added to the residue, a pH of 6 is established using 20% strength sodium hydroxide solution, and the mixture is subjected to steam distillation. During the distillation, a constant pH of 6 is maintained in the distillation flask by continuously adding 20% strength sodium hydroxide solution. The distillate is extracted three times using 100 ml of methylene chloride each time. The combined extracts are concentrated on a rotary evaporator, and 26.6 g (83% of theory) of a mixture of 82% of 2-chloro-5-methylpyridine and 18% of 2-chloro-3-methylpyridine is obtained. $^1$H-NMR spectra prove the structure.

$^1$H-NMR (CDCl$_3$), 200 MHz): δ=8.16 (6-H, ddq), 7.43 (4-H, ddq), 7.16 (3-H, br.d.), 2.26 ppm (CH$_3$, br.s.).

The pure 2-chloro-5-methylpyridine can be separated off by fractional distillation.

PREPARATION EXAMPLE 2

2-Chloro-5-methylpyridine

A solution of 92.2 g (0.375 mol) of N,N-diisobutyldichlorophosphoramide and 37.9 g (0.375 mol) of diisopropylamine in 150 ml of chlorobenzene is added dropwise under nitrogen to a solution of 27.3 g (0.25 mol) of 3-methylpyridine 1-oxide in 400 ml of chlorobenzene in such a way that the internal temperature does not exceed 35° C. When the addition is complete, stirring is continued for 15 hours at room temperature, the batch is heated for 4 hours under reflux, the solids are then filtered off with suction, the filter cake is washed once using 50 ml of chlorobenzene, and the solvent is distilled off in vacuo (50 mbar) on a 40 cm packed column. 100 ml of water are added to the residue, a pH of 6 is established using 20% strength sodium hydroxide solution, and the mixture is subjected to steam distillation. During the distillation, a constant pH of 6 is maintained in the distillation flask by continuously adding 20% strength sodium hydroxide solution (monitoring with pH electrode). The distillate is extracted three times using 100 ml of methyl tert-butyl ether each time. The combined extracts are concentrated on a rotary evaporator, and 23.8 g (75%) of a product mixture are obtained which, according to the gas chromatogram, has the following composition:

5% by weight of chlorobenzene
2% by weight of diisobutylamine,
11% by weight of 2-chloro-3-methylpyridine
82% by weight of 2-chloro-5-methylpyridine.

PREPARATION EXAMPLE 3

2-Chloro-5-methylpyridine 50.6 g (0.5 mol) of dipropylamine are added dropwise at room temperature under nitrogen in the course of 40 minutes to a solution of 115.0 g (0.75 mol) of phosphoryl chloride in 200 ml of chlorobenzene in such a way that the temperature does not exceed 60° C. The mixture is heated for 24 hours under reflux, and 25 g are then distilled off (head temperature 122°–128° C). The reaction solution and 50.6 g (0.5 mol) of diisopropylamine are simultaneously added dropwise in the course of 100 minutes to a solution, at 60° C., of 36.0 g (0.33 mol) of β-picolin-N-oxide in 130 ml of chlorobenzene. The mixture is heated for 2 hours at 60° C. and the diisopropylamine hydrochloride is filtered off with suction and washed with 50 ml of chlorobenzene. The filtrate is stirred for 1 hour with 200 ml of half-concentrated hydrochloric acid, and the aqueous phase is then adjusted to pH 6 using concentrated sodium hydroxide solution and extracted twice using 100 ml of toluene each time. After the solvent has been distilled off, 31.1 g of a mixture of 81% of 2-chloro-5-methylpyridine and 19% of 2-chloro-3-methylpyridine are obtained.

PREPARATION EXAMPLE 4

2-Chloro-5-methylpyridine 81.5 g (0.5 mol) of ethyl dichlorophosphate and 50.6 g (0.5 mol) of diisopropylamine are simultaneously added dropwise at 25° C. in the course of 45 minutes with cooling and under nitrogen to a solution of 27.3 g (0.25 mol) of β-picolin-N-oxide in 250 ml of chlorobenzene. Stirring is then continued for 3 hours at room temperature, the solids are filtered off with suction, the filter cake is washed with 50 ml of chlorobenzene and the chlorobenzene solution is subjected to fractional distillation. 22.2 g (70%) of a mixture of 81% of 2-chloro-5-methylpyridine and 19% of 2-chloro-3-methylpyridine are obtained.

We claim:

1. Process for the preparation of substituted 2-chloropyridine derivatives of the formula (I)

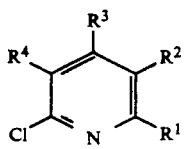
(I)

in which

R$^1$ represents hydrogen, chlorine, cyano, carbalkoxy(C$_1$-C$_4$) or

where R$^5$ and R$^6$ are identical or different and represent hydrogen or alkyl (C$_1$-C$_4$), R$^2$ represents hydrogen, chlorine, alkyl(C$_1$-C$_4$), halogenoalkyl(C$_1$-C$_4$), cyanoalkyl(C$_1$-C$_4$), alkoxy(C$_1$-C$_4$)-alkyl(C$_1$-C$_4$), dialkylamino(C$_1$-C$_4$)alkyl(C$_1$-C$_4$), carbalkoxy(C$_1$-C$_4$) or

where R$^5$ and R$^6$ are identical or different and represent hydrogen or alkyl (C$_1$-C$_4$)

or where R$^1$ and R$^2$ together represent the bivalent group —CH=CH—CH=CH—,

R$^3$ represents hydrogen, chlorine, carbalkoxy(C$_1$-C$_4$) or

where R$^5$ and R$^6$ are identical or different and represent hydrogen or alkyl (C$_1$-C$_4$), and R$^4$ represents hydrogen, chlorine or cyano, or where R$^3$ and R$^4$ together represent the bivalent group —CH=CH—CH=CH—, wherein pyridine 1-oxides of the formula (II)

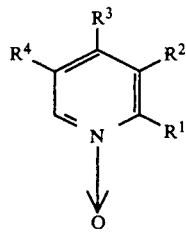

in which

R$^1$, R$^2$, R$^3$ and R$^4$ have the abovementioned meaning are reacted with a chlorine-containing phosphoric acid derivative from the series of the chlorophosphoric esters and chlorophosphoramides in the presence of an inert organic solvent and in the presence of an acid acceptor at temperatures between −20° C. and 200° C., and the resulting product is separated further, if appropriate.

2. Process according to claim 1, wherein in the reaction monoalkyl chlorophosphate,
dialkyl chlorophosphate,
cycloalkyl chlorophosphate,
aryl chlorophosphate,
diaryl chlorophosphate,
N-monoalkyl-chlorophosphoramide,
N,N-dialkyl-chlorophosphoramide,
N,N,N′,N′-tetralkylchlorophosphoric diamide,
N-cycloalkyl-chlorophosphoramide,
N-aryl-chlorophosphoramides and
N,N-diaryl-chlorophosphoramide is employed as the chlorine-containing phosphoric acid derivative.

3. Process according to claim 1, wherein a basic organic nitrogen compound from the group consisting of the dialkylamines, trialkylamines, dialkylcycloalkylamines, dialkylaralkylamines, dialkylarylamines and dialkylpyridines is employed as the acid acceptors.

4. Process according to claim 1, wherein diisopropylamine is employed as the acid acceptor.

5. Process according to claim 1, wherein methylene chloride, chloroform or chlorobenzenes are employed as the inert organic solvents.

6. Process according to claim 1, wherein the reaction is carried out at temperatures between 0° C. and 150° C.

7. Process according to claim 1, wherein an equimolar mixture of 1 to 10 moles of a chlorophosphoric ester or chlorophosphoramide and an amine in each case is added dropwise to a solution of 1 mole of the substituted pyridine-N-oxide of the formula (III) in a diluent, in a diluent, and the reaction mixture is stirred for several hours.

8. Process according to claim 1, wherein the reaction mixture formed in the reaction is distilled, extracted or subjected to steam distillation.

9. Process according to claim 1, wherein 3-methylpyridine-1-oxide is reacted with N,N-dialkyldichlorophosphoramide or alkyl dichlorophosphate in methylene chloride or chlorobenzene with the addition of diisopropylamine as the acid acceptor, for the preparation of 2-chloro-5-methyl-pyridine.

* * * * *